United States Patent [19]

Peer et al.

[11] 4,302,599

[45] Nov. 24, 1981

[54] PROCESS FOR NITRATING ANILIDES

[75] Inventors: Lydia Peer, West Orange, N.J.; Joseph Mayer, New York, N.Y.

[73] Assignee: Schering Corporation, Kenilworth, N.J.

[21] Appl. No.: 73,838

[22] Filed: Sep. 10, 1979

[51] Int. Cl.³ .................... C09B 87/60; C09B 91/06
[52] U.S. Cl. .................................. 564/146; 564/414
[58] Field of Search ............... 260/577, 562 R, 578; 564/146, 414

[56] References Cited

U.S. PATENT DOCUMENTS

| | | | |
|---|---|---|---|
| 1,963,598 | 6/1934 | Tinker et al. | 564/146 |
| 2,406,578 | 8/1946 | Bart | 564/146 |
| 2,459,002 | 1/1949 | Parker et al. | 564/146 X |
| 3,944,612 | 3/1976 | Bil | 260/578 X |
| 3,981,933 | 9/1976 | Cook et al. | 260/562 R X |

OTHER PUBLICATIONS

Morrison and Boyd, "Organic Chemistry", 3rd Ed., Allyn and Bacon, Inc., Boston (1975), p. 671.

*Primary Examiner*—Paul F. Shaver
*Attorney, Agent, or Firm*—Paul H. Ginsburg

[57] ABSTRACT

This invention describes a novel process whereby meta-substituted anilides are nitrated in the para position in high yields.

11 Claims, No Drawings

PROCESS FOR NITRATING ANILIDES

This invention relates to a process for para nitrating certain meta-substituted anilides. Additionally this invention relates to the facultative step of hydrolyzing the para-nitro-meta substituted anilides to their corresponding para-nitro-meta substituted anilines. The anilides produced by the process of this invention are known compounds, known to be useful as antiandrogenic, antibacterial and herbicidal agents. The corresponding anilines are known compounds useful as intermediates in the chemical arts.

It is generally known in the art that unsubstituted anilides may be nitrated in the para position in high yields. However, prior to this instant invention, the processes employed for para nitrating meta-substituted anilides caused the coproduction of ortho and meta nitrated products along with the desired para-nitrated product. These ortho and meta nitrated products had to be separated out, thereby causing considerable loss in yield and process efficiency with a resultant increase in cost. It is also known in the art that the use of oleum in nitration reactions will give rise to increased yields. However, it has not been known that oleum would influence the position wherein the nitration would take place.

Quite unexpectedly, we have discovered a process to para-nitrate a meta-substituted anilide in such manner as to eliminate or minimize co-production of ortho- or meta-nitrated side products. Thus, our process produces the p-nitro-m-substituted anilides in high yields without any loss of overall efficiency and at a lesser cost.

More specifically, this invention is the process for para-nitrating meta-substituted anilides which comprises subjecting said meta-substituted anilides to a mixed acid solution consisting of nitric acid and oleum under controlled conditions. In practice, the nitric acid is present at from 1 to about 4.5 moles per mole of the anilide and the oleum, having a sulfur trioxide content of from about 5% to about 40% by weight, is present at from about 1.5 to about 10 ml per gram of the anilide. The reaction is generally conducted within the temperature range of about $-20°$ C. to about $50°$ C. For a preferred mode, the nitration is carried out within the temperature range of from $-10°$ C. to about $15°$ C., the oleum has a sulfur trioxide content of about 10–30% by weight and is present at about 2.5 to 7 ml per gram of anilide, and the nitric acid is employed at about 1 to 1.2 moles per mole of anilide. The reaction time is generally about 1½ to 2 hours.

In general, the process of this invention is effected by suspending or dissolving a meta-substituted anilide (I) in oleum and under carefully controlled temperature conditions (about $0°$ C.), adding the desired amount (preferably stoichiometric amounts) of nitric acid to the anilide whilst keeping the reaction mixture under constant stirring. The reaction is permitted to proceed to completion at temperatures in the range of about $-20°$ C. to $50°$ C. The isolation of the so-obtained anilide (II) may be effected by techniques generally known and utilized for this purpose. Usually the product of the nitration is isolated by addition of the reaction mixture to an ice-water mixture with vigorous stirring. The product is collected by filtration, water-washed, dried and crystallized from the appropriate solvent. The product may also be extracted with a non-immiscible organic solvent such as methylene chloride, chloroform, benzene, ethyl acetate, ethyl ether or the like. The extract is washed, the volume reduced to a crystalline mass and the product collected by filtration. In those instances wherein an inert water immiscible solvent is used in the reaction medium, the product is obtained by washing the solvent layer with water until it is free of excess acid and by removal of the solvent to yield a crystalline mass which may be collected by filtration or centrifugation.

Modification of the foregoing may be employed without departing from the spirit and scope of this invention. For instance, if small quantities of anilide are to be nitrated it may be desirable to dissolve the nitric acid in sulfuric acid (which in some cases may also reduce exothermicity) before the nitric acid is added to the anilide/oleum mixture. For the most part, however, and particularly in larger scale production, it is preferred to use the nitric acid undiluted with sulfuric acid.

In another modification, the nitric acid-oleum mixture is prepared and the meta-substituted anilide added to the mixture with stirring. This alternate procedure is especially advantageous for the nitration of meta-substituted anilides wherein the meta-substituent is a member of the group consisting of halogen and lower alkyl.

In still another modification, the anilide may be dissolved in an inert organic solvent and the reaction effected in the usual manner. Exemplary of those solvents which do not affect the nitration (nor are they affected thereby) are nitrobenzene and chlorobenzene.

The process of this invention may be schematically depicted as follows:

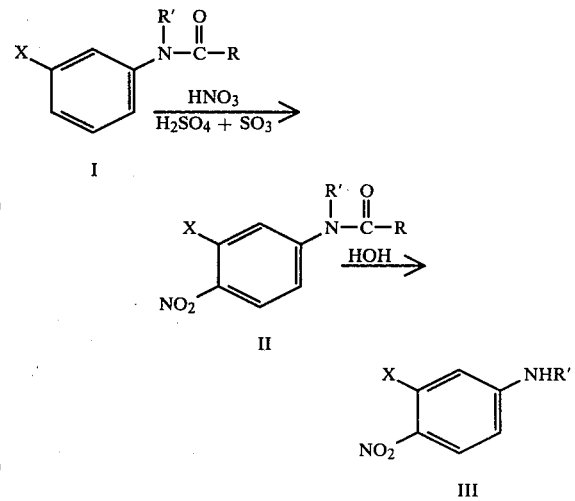

wherein the meta X-substituent is a member selected from the group consisting of halogen, nitro, polyfluoroloweralkyl, lower alkyl, and lower acyl, R is a saturated lower aliphatic hydrocarbyl having up to 12 carbon atoms, including the straight, branched-chain and cyclic manifestations thereof, and R' is hydrogen or lower alkyl. (The use of the term "lower" as it modifies alkyl and acyl includes those moieties having up to 6 carbon atoms.)

When desired, the hydrolysis of the anilides (II) may be effected under acidic or under alkaline conditions and is usually effected in a medium consisting of water, a miscible organic solvent and an alkali such as an alkali metal or an alkaline earth metal hydroxide or carbonate. When effected under acidic conditions, a strong organic acid or a strong inorganic acid is employed; such acids as alkyl or aryl sulfonic acids or hydrochloric, sulfuric, phosphoric acids or the like being preferred.

The product of the hydrolysis step is, advantageously, isolated from the reaction mixture by precipitation. The precipitate is washed, dried and crystallized from an appropriate solvent. Alternatively, the product may be extracted with an immiscible solvent, the solution washed with water and evaporated to yield the corresponding aniline derivative.

The invention described hereinabove is illustrated in detail hereinbelow in the Examples which is not to be construed as limiting the scope of our invention.

EXAMPLE 1

3'-Trifluoromethyl-4'-Nitro-Isobutyranilide

Add portion-wise 57.5 g. of m-trifluoromethyl isobutyranilide to 260 ml. of 15–18% oleum while maintaining the internal temperature at about 5° C. To this mixture add drop-wise 20 g. of 90% nitric acid with stirring. Stir at about 5° C. for 2 hours and pour into about 1½ liters of ice and water with stirring. Collect the 3'-trifluoromethyl-4'-nitro-isobutyranilide by filtration and wash with water until substantially free of excess acid.

EXAMPLE 2

3-Trifluoromethyl-4-Nitro-Aniline

Dissolve 10 g. of 3'-trifluoromethyl-4'-nitro-isobutyranilide obtained in Example 1 in 55 ml. of ethyl alcohol. Add 6 g. of 50% sodium hydroxide solution and heat the mixture to reflux. Hold at reflux for 2½ hours and pour into 500 ml. of ice-water. Collect the title compound by filtration, wash thoroughly with cold water and dry to obtain thereby 3-trifluoromethyl-4-nitroaniline.

By subjecting the products of the following examples to substantially the procedure set forth in Example 2, the corresponding meta-X-substituted-para-nitro anilines may be obtained.

EXAMPLE 3

3'-Bromo-4'-Nitro-Isobutyranilide

Prepare a solution of 260 ml. of 30–33% oleum and 20 g. of 90% nitric acid. Cool the solution to 0° and add in small portion 60.5 g. of metabromo isobutyranilide. Maintain the reaction at 0°–5° C. for an additional 30 minutes with agitation. Isolate the product by the procedure described in Example 1 to obtain 3'-bromo-4'-nitro-isobutyranilide.

EXAMPLE 4

3'-Acetyl-4'-Nitro-Isobutyranilide

Add portion-wise 16.4 g. of m-acetyl-isobutyranilide to a solution of 44 milliliters of concentrated sulfuric acid and 62 milliliters of oleum (30–33%) while maintaining the internal temperature at 0°–5° C. Cool the mixture to −8° C. and add drop-wise 65 milliliters of 90% nitric acid. Stir the reaction mixture at 0°–5° C. for an additional 40 minutes and precipitate the product as described in Example 1 to obtain 3'-acetyl-4'-nitro-isobutyranilide.

EXAMPLE 5

3'-Trifluoromethyl-4'-Nitro-3-Methylvaleranilide

Add portion-wise 54 g. of m-trifluoromethyl-3-methylvaleranilide to 250 ml. of oleum (30–33%) while maintaining the temperature at 0°–5° C. To this mixture add 17 g. of 90% nitric acid. Stir the mixture for one hour at 0°–5° C. and precipitate as described in Example 1 to obtain thereby 3'-trifluoromethyl-4'-nitro-3-methyl-valeranilide.

EXAMPLE 6

3'-Trifluoromethyl-4'-Nitro-Acetanilide

To 250 ml. of 15% oleum, add portion-wise 47.7 g. of m-trifluoromethyl acetanilide while maintaining the internal temperature at 0°–5° C. To this mixture add 19 g. of 90% nitric acid in 45 ml. of concentrated sulfuric acid. Stir the mixture at about 0°–5° C. for 2 hours and precipitate as described in Example 1 to obtain thereby 3'-trifluoromethyl-4'-nitroacetanilide.

EXAMPLE 7

3'-Methyl-4'-Nitro-Isobutyranilide

Prepare a solution of 260 ml. of 15% oleum and 20.3 g. of 90% nitric acid. Cool the solution to 3°–5° C., and add in small portions 44.3 g. of N-isobutyryl-m-toluidine. Maintain the reaction at 3°–5° C. for an additional 15 minutes with agitation. Isolate the product by the procedure described in Example 1 and obtain thereby 3'-methyl-4'-nitro-isobutyranilide.

EXAMPLE 8

3'-Fluoro-4'-Nitro-Isobutyrylanilide

Prepare a solution of 260 ml. of 20% oleum and 20.3 g. of 90% nitric acid. Cool the solution to 0° C. and add in small portions 45.5 g. of metafluoro-isobutyranilide. Maintain the reaction at 0°–5° C. for an additional 30 minutes with agitation. Isolate the product by the procedure described in Example 1 and obtain thereby 3'-fluoro-4'-nitro-isobutyranilide.

EXAMPLE 9

3',4'-Dinitro-Isobutyrylanilide

Prepare a solution of 52 g. of m-nitro-isobutyrylanilide in 260 ml. of 15% oleum and cool to 0°–5° C. Add drop-wise with agitation 61.5 g. of 90% nitric acid to the solution while maintaining the temperature at 0°–5° C. Continue the reaction for an additional hour and isolate the product as described in Example 1 to obtain 3',4'-dinitro-isobutyranilide.

EXAMPLE 10

3'-Chloro-4'-Nitro-Isobutyranilide

Prepare a solution of 260 ml. of 15% oleum and 20.3 g. of 90% nitric acid, adjust the temperature of the solution to 0° C. and add in small portions 49.5 g. of meta-chloro-isobutyranilide. Maintain the reaction at 0°–5° C. for an additional hour with agitation. Isolate the product by the procedure described in Example 1 and obtain thereby 3'-chloro-4'-nitro-isobutyranilide.

We claim:

1. The process for para nitrating a meta-substituted anilide wherein the meta-substituent is selected from the group consisting of lower alkyl, lower acyl, polyfluoro lower alkyl, nitrogen and halogen; which comprises subjecting said meta-substituted anilide to a mixed acid solution consisting of nitric acid and oleum wherein the reaction temperature is maintained at from about −20° C. to about 50° C., the nitric acid is present at from about 1 to about 4.5 moles per mole of anilide and the oleum is present at from about 1.5 to about 10 milliliters per gram of anilide.

2. The process according to claim 1 including the steps of isolating and hydrolyzing the para-nitro-meta-substituted anilide to yield the corresponding meta-substituted-para-nitro aniline.

3. The process according to claim 1 wherein the oleum has a sulfur trioxide content by weight of from about 5% to about 40%.

4. The process of claim 3 wherein the nitric acid is present at from about 1 to about 1.2 moles per mole of anilide and the oleum is present in the ratio of from about 2.5 to about 7 milliliters per gram of anilide.

5. The process of claim 4 wherein the nitrating step is conducted for from about ½ to about 2 hours and the sulfur trioxide constitutes from about 10% to about 25% by weight of the oleum.

6. The process of claim 2 wherein m-trifluoromethylisobutyranilide is nitrated to produce 3'-trifluoromethyl-4'-nitroisobutyranilide and hydrolyzing said compound to yield 3-trifluoromethyl-4-nitro aniline.

7. The process of claim 1 wherein m-trifluoromethyl isobutyranilide is nitrated to produce 3'-trifluoromethyl-4'-nitro isobutyranilide.

8. The process of claim 1 wherein m-chloro isobutyranilide is nitrated to produce 3'-chloro-4'-nitro isobutyranilide.

9. The process of claim 1 wherein m-bromo isobutyranilide is nitrated to produce 3'-bromo-4'-nitro isobutyranilide.

10. The process of claim 1 wherein m-fluoro isobutyranilide is nitrated to produce 3'-fluoro-4'-nitro isobutyranilide.

11. The process of claim 1 wherein m-nitro isobutyranilide is nitrated to produce 3',4'-dinitro isobutyranilide.

* * * * *